United States Patent
Appel

(10) Patent No.: US 8,348,961 B2
(45) Date of Patent: Jan. 8, 2013

(54) GASTRIC BAND INTRODUCER

(75) Inventor: Sidney Appel, Atlanta, GA (US)

(73) Assignee: Automated Medical Products Corporation, Sewaren, NJ (US)

( * ) Notice: Subject to any disclaimer, the term of this patent is extended or adjusted under 35 U.S.C. 154(b) by 1047 days.

(21) Appl. No.: 11/475,106

(22) Filed: Jun. 27, 2006

(65) Prior Publication Data

US 2007/0088191 A1    Apr. 19, 2007

Related U.S. Application Data

(63) Continuation-in-part of application No. 11/250,384, filed on Oct. 17, 2005, now abandoned.

(51) Int. Cl.
*A61F 2/00* (2006.01)

(52) U.S. Cl. .................. 606/140; 600/37; 606/148

(58) Field of Classification Search .............. 606/140, 606/148, 139, 141, 144, 145, 146; 600/29, 600/30, 37; 124/17, 18, 20.1
See application file for complete search history.

(56) References Cited

U.S. PATENT DOCUMENTS

| | | | | |
|---|---|---|---|---|
| 4,580,560 A | * | 4/1986 | Straith | 606/108 |
| 4,592,355 A | * | 6/1986 | Antebi | 606/144 |
| 5,449,368 A | * | 9/1995 | Kuzmak | 606/157 |
| 5,658,298 A | | 8/1997 | Vincent et al. | 606/139 |
| 7,060,080 B2 | | 6/2006 | Bachmann | 606/151 |
| 7,144,400 B2 | | 12/2006 | Byrum et al. | 606/140 |
| 2003/0216759 A1 | * | 11/2003 | Burbank et al. | 606/157 |
| 2004/0204718 A1 | * | 10/2004 | Hoffman | 606/108 |
| 2005/0075652 A1 | * | 4/2005 | Byrum et al. | 606/139 |
| 2006/0200175 A1 | * | 9/2006 | Griffiths | 606/139 |

FOREIGN PATENT DOCUMENTS

EP    1 281 360    2/2003

OTHER PUBLICATIONS

International Search Report PCT/US06/40714.

* cited by examiner

*Primary Examiner* — S. Thomas Hughes
*Assistant Examiner* — Julie A Szpira
(74) *Attorney, Agent, or Firm* — Dorsey & Whitney LLP

(57) ABSTRACT

A surgical introducer for an implant, such as a gastric band. The introducer has a shaft portion with a longitudinal axis extending through proximal and distal sides. A guide bore extends longitudinally through the shaft portion to extend the shaft to slide over an elongated guide member. A band-pulling member is disposed on the distal side and is configured to retain the implant in a loaded position on the shaft and to pull the implant in this position across an incision, such as across an abdominal wall, through an implantation site.

24 Claims, 5 Drawing Sheets

GASTRIC BAND INTRODUCER

CROSS-REFERENCE TO RELATED APPLICATIONS

This is a continuation-in-part of U.S. application Ser. No. 11/250,384, filed Oct. 17, 2005, now abandoned the entire content of which is hereby incorporated by reference thereto.

FIELD OF THE INVENTION

The present invention relates to a surgical introducer for a surgical implant. More particularly, the present invention relates to a surgical introducer for inserting an implant, such as a gastric band, preferably into the abdomen of a patient.

BACKGROUND OF THE INVENTION

A known bariatric surgical procedure involves placing a gastric band around a portion of the stomach, using laparoscopic techniques. This surgery is used for treatment of morbid obesity, and accomplishes a gastric bypass, in which the upper stomach outlet is restricted, to slow the food passage into the lower stomach. One location for placement of the gastric band is at the esophageal jejunum.

One successful gastric band is made by Innomed, Inc. under the trade name LAP-BAND®. The LAP-BAND® gastric band is made of silicon and is inflatable to control the degree of restriction about the upper stomach outlet. Typically, the gastric band is introduced intraperitoneally and is maneuvered about the stomach using an articulating dissector. Other surgical instruments that have been used to introduce the gastric band to the implantation site include solid rods with a hook either on the side of the rod, such as sold by Richard Wolf Medical Instruments Corporation, or with a notch on the tip of the rod to pull the band by an opening provided at the front of the band.

During the above bariatric procedure, different instruments and laparoscopic cameras can be inserted and removed through cylindrical ports that are placed through the abdominal wall. Since the abdomen is insufflated, insertion of certain instruments causes the loss of insufflation. Other instruments, such as the traditional gastric band introducers, are inserted once the port is removed, directly through the incision in the abdominal wall. Since the tissue around the incision naturally closes, the insertion of the introducer with the loaded gastric band becomes very difficult, needing to be forced through the tightly closed incision. Additionally, the rear portion of the band that extends outside of the patient must be controlled by the surgeon during insertion so that the band does not slide off the hook of the introducer.

Thus, an improved gastric band introducer is needed, which can facilitate insertion through the abdominal wall and the control of the gastric band while it is maneuvered into position.

SUMMARY OF THE INVENTION

The invention relates to a surgical introducer for inserting an implant, such as a gastric band, to an implantation site. A preferred embodiment of the introducer has a shaft portion that has a longitudinal axis extending trough proximal and distal sides of the shaft portion. A guide bore extends longitudinally with respect to the shaft portion to guidedly receive and slide over an elongated guide member. Although the preferred implant to be used is a gastric band, other types of implants may be employed with the invention. In the preferred environment, a band-pulling member is disposed on the distal side and is configured to retain the band in a loaded position on the shaft. In this position, the band-pulling member can pull the gastric band through an incision across an abdominal wall to an implantation site. Preferably, this is done with the band mounted externally with the shaft portion.

The preferred guide bore is eccentric with respect to the shaft portion. The preferred shaft portion has an exterior surface that includes a band-accommodating surface. The band-accommodating surface is preferably configured to reduce the profile height in a radial direction of the band in the loaded position. The band-accommodating surface can have a flattened shape in a lateral direction and preferably is disposed and has a configuration for stabilizing the band in the loaded position. The shaft portion of the preferred embodiment has a curved surface portion with a first radius of lateral curvature. The band-accommodating surface has a second radius of lateral curvature that is greater than the first radius of curvature, and can be flat. The notch is configured and dimensioned to receive a protrusion of the band to further reduce the protruding height of the band above the shaft portion in the loaded position. The notch has a preferred width measured in the longitudinal direction of between about 10 mm and 5 mm, and is preferably between about 0.5 mm to 2 mm deep. The band-pulling member preferably has a band seat that is engaged with the band in the loaded position to pull the band to the incision. The notch is preferably positioned to receive the protrusion of the band located between about 1 cm and 2 cm proximally from the pulling-member seat.

The pulling member preferably comprises a hook that extends radially from the band-accommodating surface. A notch is defined in the preferred band-accommodating surface and is disposed proximally from the band-pulling member. On its distal side, and preferably on the distal end, the preferred shaft portion has a forward portion. The forward portion is disposed distally from the band-accommodating surface and is elevated with respect thereto. Additionally, the forward portion has a tapered configuration to facilitate insertion into the incision about the guide member. The band-pulling member preferably extends from the collar-accommodating surface to a height that is lower than the height of the forward portion measured in a radial direction. Most preferably, the forward portion has a bullet-nose configuration.

The preferred introducer also has a retaining member that is disposed on the proximal side of the shaft portion and is configured for engaging and retaining another portion of the band that is remote from the portion engaged with the pulling member. The retaining member preferably extends radially from shaft portion and defines a tapered groove for wedging this portion of the band therein. The location of the retaining member on the shaft portion is also preferably selected so that the retaining member remains outside the patient when the distal end of the shaft portion is disposed inside the patient's abdomen in a position in which the band has been sufficiently introduced to be grasped and maneuvered by other surgical instruments.

Most preferably, the introducer is configured to introduce the band or other implant in the loaded position in which the implant is mounted externally on the shaft portion and externally to the introducer. Also, the guide member is preferably inserted in the guide bore and placed into the incision prior to sliding the shaft member thereover, to both maintain alignment of the incision through the plurality of tissue layers and to maintain the incision in an open position, since tissue naturally tends to close about the incision. While a preferred guide member is made of stainless steel, in one embodiment, the guide member is of a flexible material to avoid or reduce the chance of damaging tissue at the implantation site for the implant, and in another embodiment, the guide member is both flexible and has a natural bend. For example, this embodiment of the guide member may tend to bend away from the longitudinal axis and may be naturally biased to a curved or curled configuration curved away from any tissue that is longitudinally ahead of the introducer.

The shaft portion can have a sloped surface on a portion ahead of the band or implant mounting portion that is configured for spreading tissue thereabout when the introducer is rotated about the longitudinal axis. The insertion-assisting surface preferably has lateral sides that are disposed further from the longitudinal axis than an intermediate portion of the insertion-assisting surface therebetween to spread tissue thereabout when the introducer is rotated about the longitudinal axis. In one embodiment, the insertion-assisting surface is substantially flat, and in another it is concave. A preferred slope angle of the insertion-assisting surface is preferably between about 10° and 60°.

The present invention thus provides an introducer that can be used with a gastric band or other implement that facilitates insertion into the patient's body.

DETAILED DESCRIPTION OF THE PREFERRED EMBODIMENTS

Figure 1:
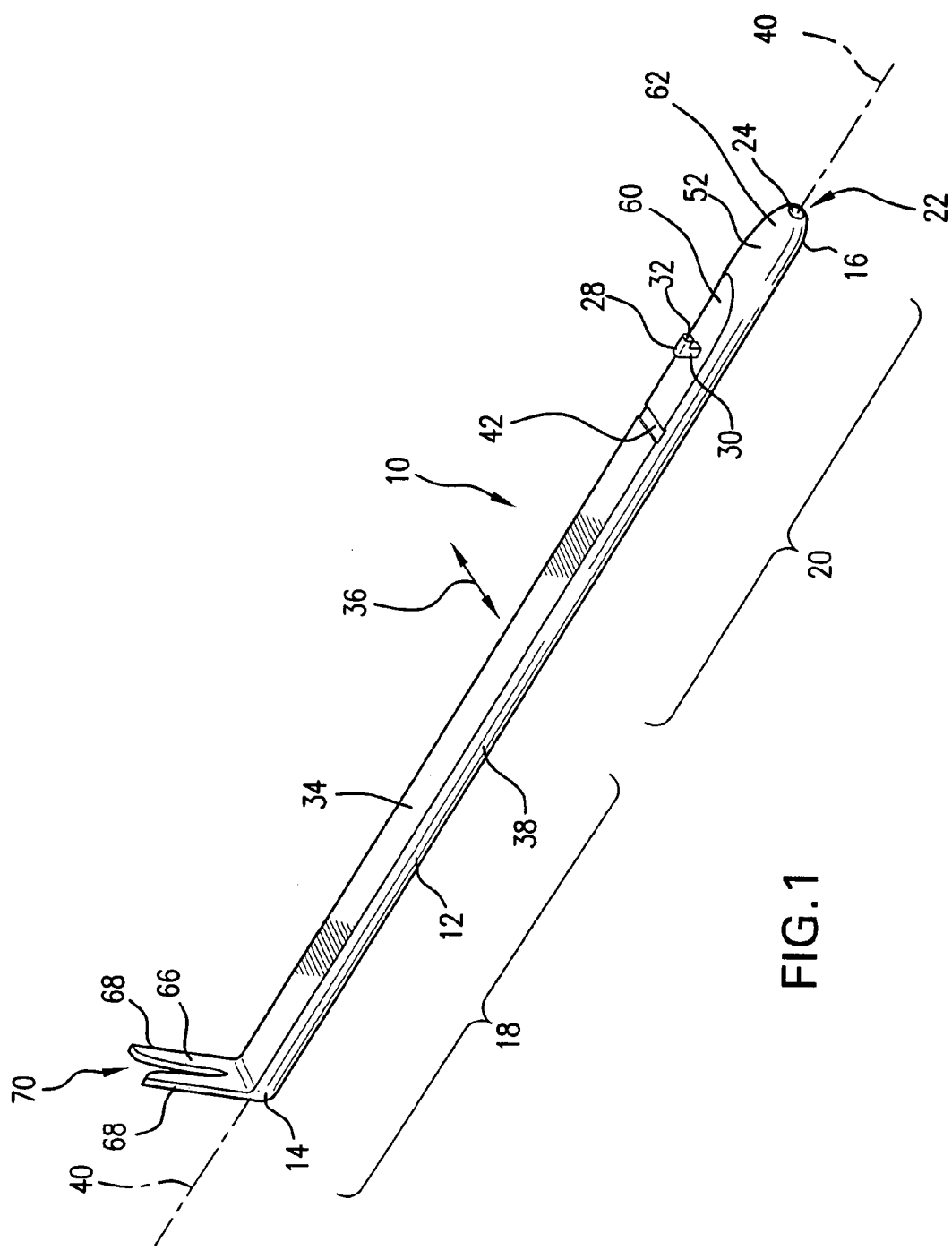
FIG. 1 is a perspective view of a preferred embodiment of a surgical introducer constructed according to the present invention.
Figure 2:
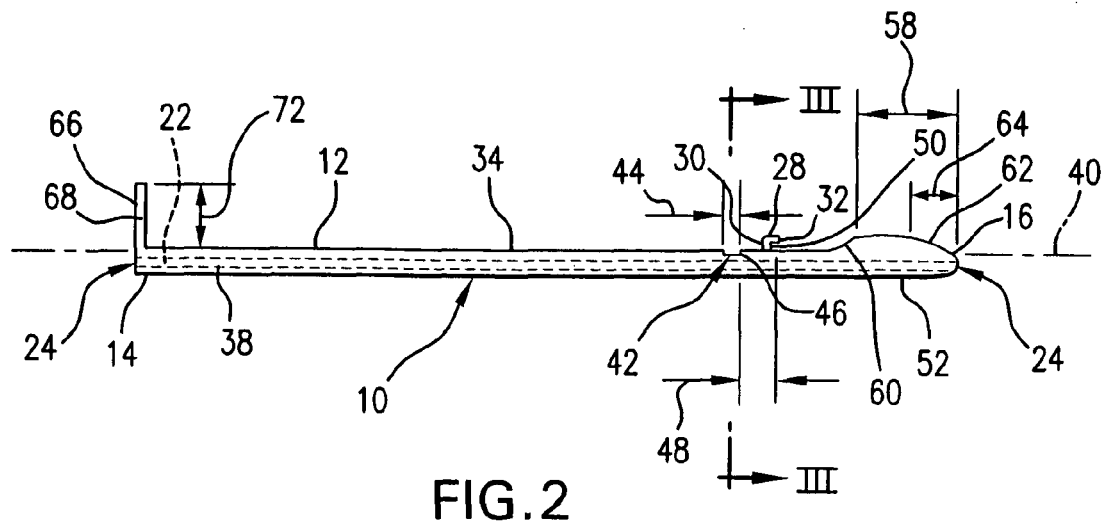
FIG. 2 is a side view thereof.

Referring to FIGS. 1 and 2, a preferred embodiment of a surgical introducer 10 that is preferably configured to introduce a band into a patient's body through an incision. The preferred introducer is configured for introducing a band into the patient's abdominal cavity, and the preferred band is a restrictive gastric band.

Introducer 10 includes a shaft portion 12 that has proximal and distal ends 14,16 disposed on proximal and distal sides 18,20 of the shaft portion 12. The preferred length of the shaft portion 12 is at least about 15 cm, and more preferably at least about 25 cm, and preferably is up to about 50 cm, and more preferably up to about 40 cm, with the length of one embodiment being around 30 cm.

Figure 3:
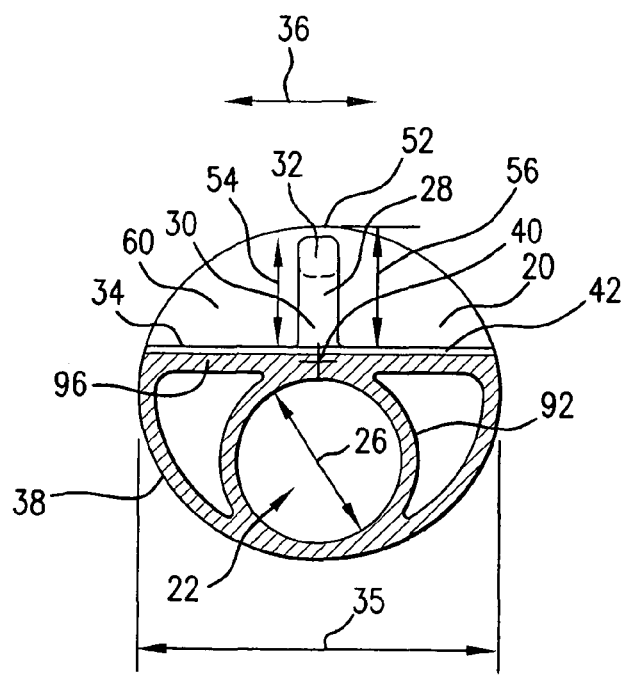
FIG. 3 is a cross-sectional, axial view taken along plane III-III of FIG. 2.

A guide bore 22 extends through the shaft portion 12, preferably longitudinally, with openings 24 at both the proximal and distal ends 14,16. The bore 22 is preferably configured and dimensioned for guidedly receiving and sliding over an elongated guide member, such as a guide rod or guide wire. In a preferred embodiment, the bore 20 has a round, and preferably circular cross-section, as shown in FIG. 3, but in alternative embodiments, the bore has a different cross-sectional shape, such as an I-shaped or S-shaped cross-section, for receiving a differently configured guide member.

Preferably, a circular bore 22 has an internal diameter 26 of at least about 2 mm, and more preferably at least about 3 mm, and at most about 8 mm, more preferably at most about 6 mm, and more preferably at most about 5 mm. One embodiment has a bore diameter 26 of around 4 mm to readily receive a 3 mm cylindrical guide rod. As shown in FIG. 3, the bore 22 has an axis that is eccentric from the longitudinal axis 40 of the shaft portion 12, although concentric axes can alternatively be provided.

A band-pulling member, which in the preferred embodiment comprises a hook 28, is disposed on the distal side 20 of the introducer 10. The hook 28 is configured for retaining the gastric band in a loaded position on the shaft portion 12 and pulling the gastric band in this position though an incision, preferably across an abdominal wall, to a desired implantation site. The hook 28 preferably has a hook base 30 connected with the shaft portion 12 and supporting a hook end 32, which extends distally. The hook end 32 is dimensioned and oriented to be inserted into a loading opening of a gastric band and directing this opening toward the hook base 30, such that the band is biased and retained in association with the hook base 30 when pulled proximally. Thus, the preferred hook 28 has an open side oriented toward the distal end 16.

Hooks with other shapes are used in alternative embodiments. In some embodiments, the band-pulling member comprises a different mechanism for holding or gripping the band, such as a clamp or clip. The preferred band-pulling member is configured to enable releasing the band therefrom interabdominally, using laparoscopic surgical instruments, such as dissectors or clamps. In the preferred embodiment, the radial thickness of the hook end 32 is around 1 mm, as is the longitudinal thickness of the hook base 30.

The shaft portion 12, preferably on its exterior, includes a band-accommodating surface 34 that can provide a bed for the band mounted thereon. In the embodiment of introducer 10, the band-accommodating surface 34 extends from the proximal to the distal sides 18,20 of the introducer 10 and is preferably uniform. The band-accommodating surface 34 of the embodiment shown is flattened in a lateral direction 36, and can be substantially flat, as shown in FIG. 3. In one embodiment, an underside 38 of the shaft portion 12, opposite the band-accommodating surface 34 has a rounded, preferably cylindrical surface, and the band-accommodating surface 34 has a greater radius of curvature than the underside measured along a lateral plane with the underside surface, preferably having a center of curvature about the longitudinal axis 40 of the shaft portion 12. In another embodiment, the band-accommodating surface is uneven, irregular, undulating, or rough, or has another shape that reduces the height at which the loaded band protrudes above the shaft portion 12 when mounted thereon. Preferably, the shape of the band-accommodating surface 34 is also selected to stabilize the mounted band during penetration across the abdominal wall. Also, while the preferred shaft portion 12 is generally rounded, at least on the underside 38, alternative embodiments have different cross-sections, such as rectangular or oval. The preferred lateral width 35 and preferably the height of the introducer 10 as well, is between about 5 mm and 2 cm, and more preferably around 1 cm.

The hook 28 of introducer 10 extends from the band-accommodating surface 34 to place the loaded band thereon. The band-accommodating surface 34 of this embodiment defines notch 42 that is disposed to receive a protruding portion of the band in the loaded position to further reduce the protruding height of the band above the shaft portion 12. The notch 42 is disposed proximally from the hook 28. The notch 42 preferably has a longitudinal width 44 of at least about 2 mm and more preferably at least around 3 mm, and up to about 1 cm, and more preferably up to about 5 mm. The depth of the notch 42 is preferably between about 0.5 mm and 2 mm, and in one embodiment is about 1 mm. The dimensions and shape of the notch 42 can be varied depending on the shape of the band intended to be used and the size of the shaft portion 12, the guide bore 22, and the location of the band-accommodating surface 34, for example. The location of the notch 42 with respect to the hook 28 can also be selected based on the particular configuration of the band to be used.

The notch 42 of introducer 10 has a distal side 46 that is disposed at a distance 48 of between about 5 mm and 2 cm proximally from the distal side 50 of the hook base 30, which provides a seat for the portion of the band that is hooked, and most preferably at between about 1 cm and 1.5 cm proximally therefrom. Preferably, the notch 42 is positioned to receive a band protrusion that is disposed between about 1 cm to 2 cm proximally of the distal side 50 of the hook base 30.

A forward portion 52 of the introducer 10 disposed at the distal end 16 has an outer surface that is elevated with respect to the band-accommodating surface 34. The height 54 of the hook 28 with respect to the longitudinal axis 40 and above the band-accommodating surface 34 is preferably no greater than the height 56 of the forward portion 52, and can be equal thereto. In some embodiments, the hook 28 can be made higher than the forward portion 52, but care should be taken to keep the hook from catching on the tissue surrounding the incision in which the introducer 10 is being inserted. When the forward portion 52 is the same height or higher than the hook 28, the forward portion 52 can protect the hook from catching or snagging on this tissue.

Forward portion 52 preferably has a tapered leading, distal side, and most preferably has a bullet-nose shape to facilitate pushing into the incision. While a radial wall can be provided on the proximal side of the forward portion 52, introducer 10 has a sloped, curving ramp 60 that leads from the outer surface of the forward portion to the band-accommodating surface 34.

The preferred forward portion 52 has a longitudinal length 58 of from about 1 cm, and more preferably up from about 2 cm, and preferably up to about 4 cm or 5 cm, and more preferably to about 3 cm. A preferred length 58 is about 2.5 cm. The tapered leading portion 62 of the forward portion 52 has a longitudinal length 64 of between about 0.5 and 2 cm, and more preferably around 1 cm.

Preferably, at or near the proximal end 14 of the shaft portion 12 is a retaining member 66 that is configured to retain a portion of the band loaded on the introducer 10 that is remote from the portion retained by the hook 28. The preferred retaining member 66 comprises two adjacent, upright extensions 68 that extend radially from the shaft portion 12 and define a gripping space 70 therebetween. The gripping space of introducer 10 is has a tapered, wedge shape so that a tail of the band can be pulled therein and wedged into engagement with the proximal side of the introducer 10, or at least proximally from the hook 28, most preferably at a location that remains outside the patient during the introduction of the band. While the height 72 of the extensions 68 can be selected based on the configuration of the band to be used and the amount of movement to be employed by the surgeon in securing the band tail into the gripping space 40.

Alternative retaining members can comprise small nubs or a longitudinal groove to capture the band, or a clip, clamp, or other member that can pinch or fasten the band to the introducer. Since the retaining member will typically remain outside the patient during the introduction of the band into the abdomen, the retaining member can be configured to be hand operated, and threaded fasteners or snaps can also be provided, for example.

Figure 4:
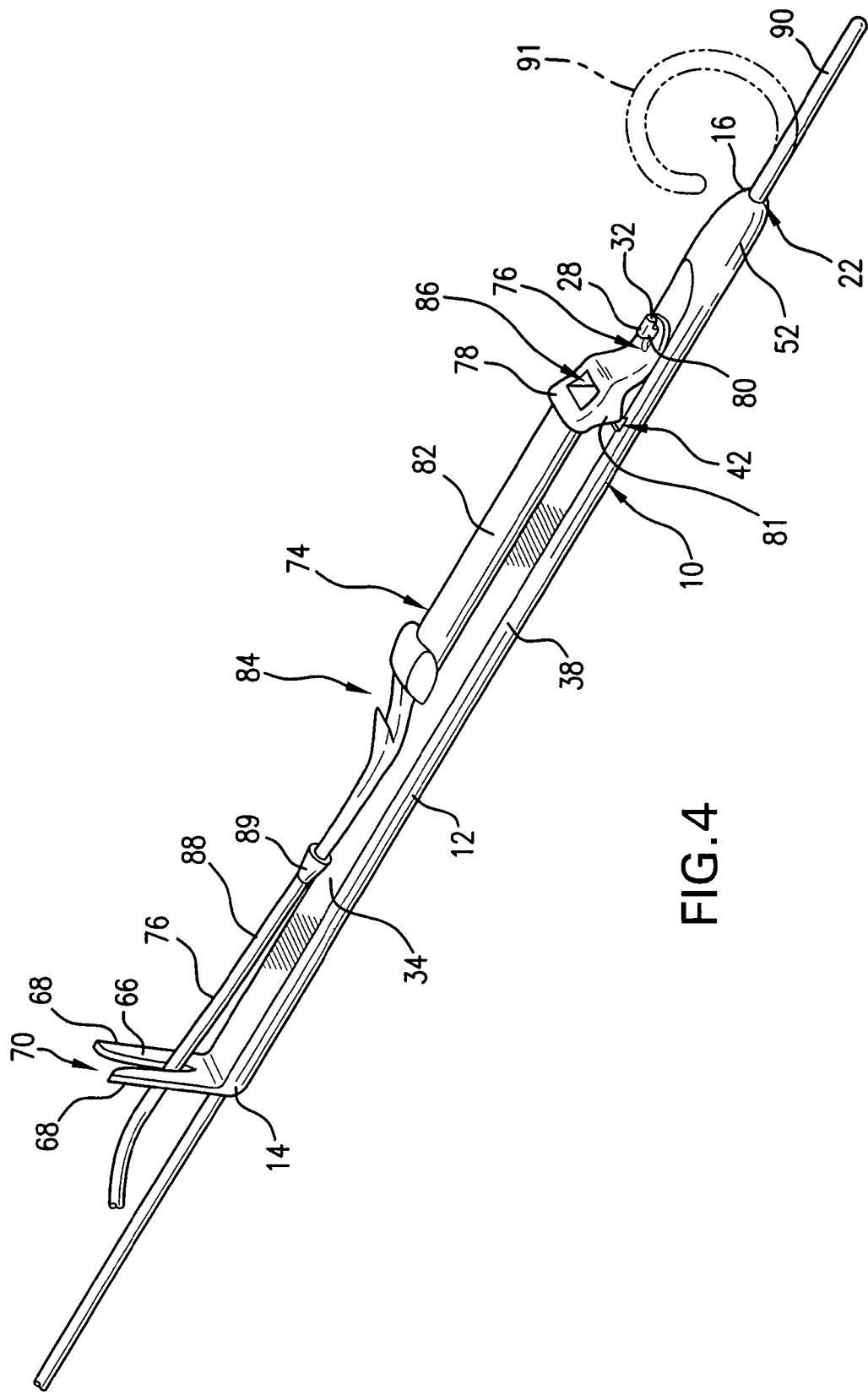
FIG. 4 is a perspective view of the introducer of FIG. 1 with an embodiment of a gastric band loaded thereon.

FIG. 4 shows a preferred embodiment of a gastric band 74, preferably made of silicone or another suitable material, loaded onto the introducer 10, externally thereto. A loading opening 76 of the band 74 is hooked on hook 28, and a tail 76 of the band 74 is engaged in the retaining member 66. The band 74 has a buckle 78 proximally from a tab 80 that defines the loading opening 76. The buckle 78 has a protrusion 81 that protrudes radially towards the shaft portion 12 and is received in the notch 42 to reduce the height to which the loaded band 74 extends above the shaft portion 12 to minimize resistance to penetration of the abdominal wall.

From the distal side to the proximal side of the band 74 from the buckle 78 is a collar portion 82 configured for placement around the stomach or other internal part of the body, a locking member 84 configured for insertion in buckle opening 86 in locked engagement therewith, and a tail 88, which can have an enlarged portion 89 to be temporarily received in the buckle opening 86 during initial placement of the band 74 at the implantation site. The tail 88 is preferably made of a hollow tube for connecting to a fluid reservoir that can be used to pump fluid into the interior of the collar 82 for inflating the balloon-type collar 82 to adjust the gastric restriction of the implanted band 74.

The introducer 10 is shown being passed over a guide rod 90. In surgery, a port incision is made in the abdomen, and a port is inserted therein to provide access to the abdominal cavity. Typical ports are around 5 mm or 10 mm in diameter. In the preferred embodiment, an 11.5 mm port is used. The guide rod 90 is inserted into the port, and the port is then removed. In this position, the guide rod 90 maintaining the various layers of tissue, including the skin and muscles, in position to maintain the alignment of the incisions made therethrough. Also, the rod 90 prevents the tissue from closing around the incision. Both misalignment of the layers of the incision and the closing of the tissue greatly facilitate the insertion of the introducer with the loaded band 74.

With the band 74 loaded onto the introducer 10, introducer 10 is then slid over the rod 90, which facilitates the penetration of the various layers of the abdominal wall. Once the distal side 20 of the band 74 in within the insufflated abdominal cavity, the band 74 is removed from the hook 28 by instruments inserted into other ports. The surgeon can then disengage the band tail 88 from the retaining member 66, and the tail 88 is then drawn into the abdominal cavity with instruments inserted into the other ports. Thereafter, the surgeon proceeds to maneuver the band 74 around the desired location such as a portion of the digestive tract, for instance the stomach, using instruments such as dissectors or grippers. Preferably, the disengagement of the band from either or both the band-pulling member, such as the hook 28, and the retaining member 66 is easily accomplished with a simple motion, such as in a single general direction, without requiring complex movements, such as rotation. More complex disengagement motion, however, can be suitable in alternative embodiments.

The introducer 10 is preferably made of surgical steel, or another suitable material. A disposable embodiment of the introducer can be made of a plastic, for example. The guide rod 90 is also preferably made of steel and is relatively rigid. In one embodiment, the guide member is made of a flexible, preferably elastic material, and can naturally be curved so that its tip will curve away from organs it would otherwise face or bend harmlessly away therefrom to help prevent damaging surrounding organs. Silicone, or an elastomeric or rubber material are suitable for the flexible and preferably soft embodiments of the guide member. An embodiment of a guide member 91 that is naturally biased to curl away from the longitudinal axis 40 is shown in FIG. 4 in phantom lines, curved distally of the introducer 10, and flexed to a straight shape within the introducer 10.

In the embodiment shown in FIG. 3, the bore 22 is provided by attaching a hollow tube 92 to an interior wall of a tube 94 from which one side has been removed up to the forward portion 52. A sheet 96 is then attached to the small and large tubes 92,94 to provide the band-accommodating surface. The hook 28 is preferably attached through an opening in the sheet 96 to the smaller tube 92. The forward end of the larger tube 94 can be reformed to provide the bullet-nose shape. While the different components are preferably welded, soldered, or otherwise adhered or fastened to each other, to form an integral structure, an introducer of unitary construction is also envisioned.

Figure 5:
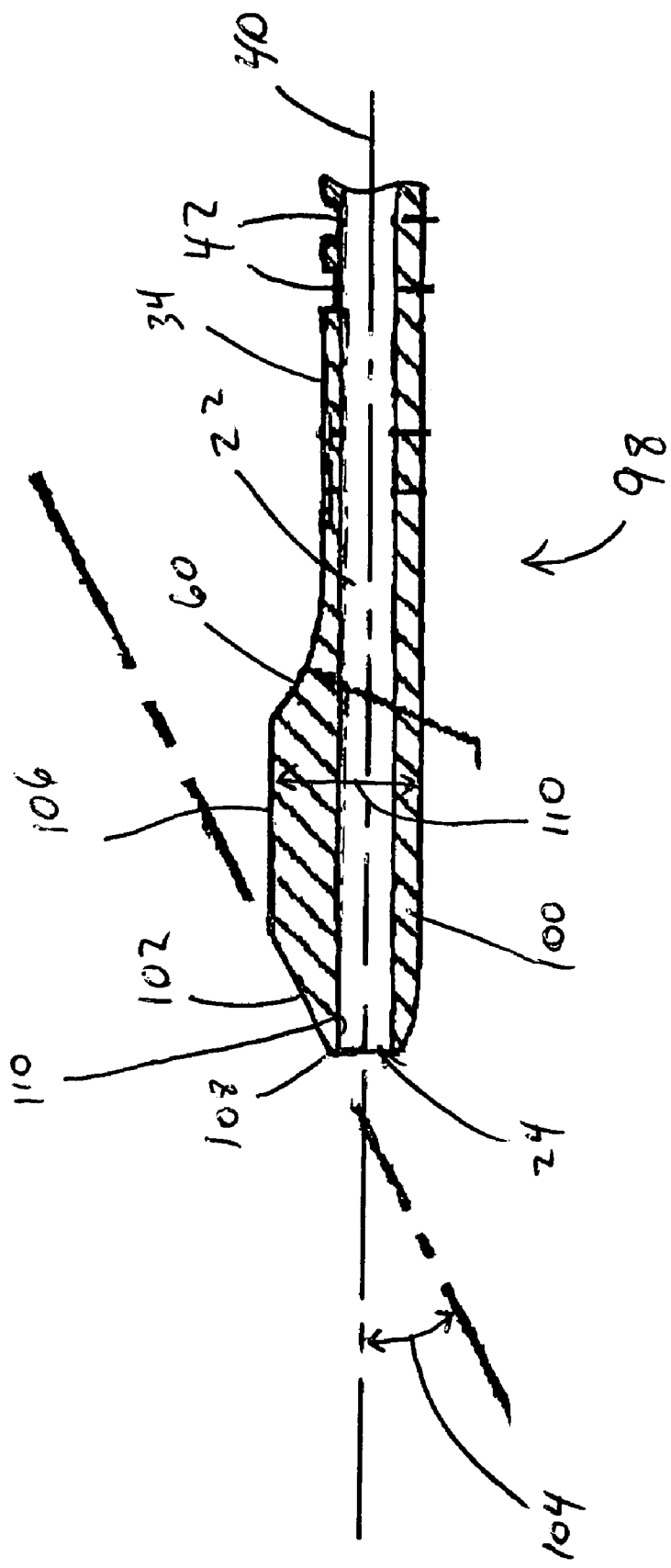
FIG. 5 is a cross-sectional, side view of a distal end of another embodiment of a surgical introducer constructed according to the present invention.
Figure 6:
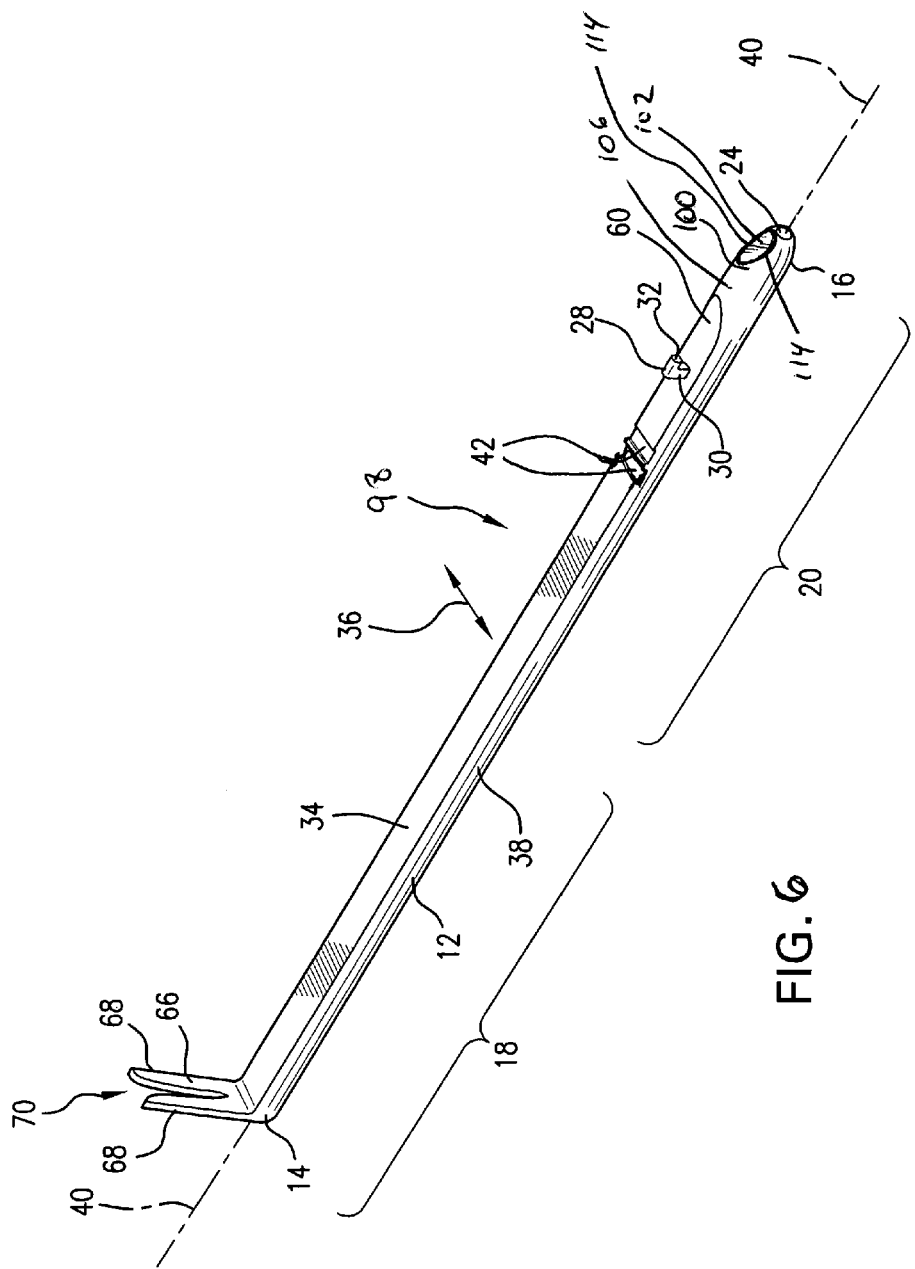
FIG. 6 is a perspective view of the embodiment of FIG. 5.

Referring to FIGS. 5 and 6, another embodiment an inventive introducer 98 with a forward, distal end 100 that has a flat, sloped insertion-assisting surface 102 that faces distally and preferably upwards. The surface 102 is preferably sloped at an angle 104 with respect to the longitudinal axis of the guide bore 22, and is preferably laterally aligned or nearly laterally aligned with the orientation of the band-accommodating surface 34, although alternative embodiment shave other orientations. The angle 104 is preferably at least about 10°, more preferably at least about 20°, and up to about 60°, and more preferably up to about 40°, and most preferably up to about 30°. In a preferred embodiment, angle 104 is around 25°.

The surface 102 has lateral sides 114 that are disposed further from the axis 40 than part or all of the surface therebetween, preferably at any longitudinal position along the surface 102. This helps spread muscle and other tissue by rotating the introducer about the guider wire and about axis 40 to facilitate insertion into an incision.

The surface 102 is substantially flat. In another embodiment, the surface 102 can by facetted or curved in a lateral direction with a radius of curvature that is larger than the distance to the axis 40 or larger than the radius of curvature of top surface 106 of the distal portion, which is preferably immediately proximal of the insertion-assisting surface 102. In other embodiments the insertion-assisting surface is concave or convex, preferably by a small amount, about a laterally extending axis. Preferably at least about the leading ⅕, more preferably ¼, and most preferably ½ of or all of the surface is oriented at angle 104. The surface 102 is preferably at or close to the forward-most portion of the introducer.

The preferred distal end 108 of insertion-assisting surface 102 meets the inner wall 110 of bore 40 or can be slightly above but near the wall. In one embodiment, the surface extends to below the top portion of the wall, resulting in a concave top side of the bore. Preferably, the longitudinal length of surface is greater than about the diameter of the bore 40 and greater than about half the height 112 of the distal portion 100. This embodiment has a plurality of notches 42 to receive multiple protrusions of a gastric band or other implant, or to receive a protrusion from one of various sizes of bands or other implants.

When inserting the introducer 98 into an incision over a guide wire, the insertion-assisting surface 102 facilitates the initial penetration into the incision. It has been found that rotating the introducer about the guide wire once the tip of the introducer 98 starts to spread apart the muscle tissue, which tends to contract about the introducer and resist its further insertion, causes the insertion-assisting surface 102 to readily spread apart the muscle, thus greatly facilitating the insertion of the introducer by significantly reducing the resistance of by the muscle.

The term "substantially," as used herein to refer to a shape, e.g., substantially semi-cylindrical or semi-circular cross-section, is intended to include variations from the true shape that do not affect the overall function of the device. The term "about," as used herein, should generally be understood to refer to both numbers in a range of numerals. Moreover, all numerical ranges herein should be understood to include each whole integer within the range.

While illustrative embodiments of the invention are disclosed herein, it will be appreciated that numerous modifications and other embodiments may be devised by those skilled in the art. Therefore, it will be understood that the appended claims are intended to cover all such modifications and embodiments that come within the spirit and scope of the present invention.

What is claimed is:

1. A surgical introducer for an implant, comprising:
   a shaft portion extending longitudinally with proximal and distal sides, the shaft portion defining a guide bore extending longitudinally through the shaft portion for guidedly receiving and sliding over an elongated guide member, the guide bore having a longitudinal axis, wherein the shaft portion has a distal end in the distal side, the bore having an a distal opening defined in the distal end along the longitudinal axis through which the bore extends longitudinally with respect to the shaft portion; and
   an implant-mounting member having an implant-accommodating surface disposed on the distal side and configured for retaining the implant in a loaded position exposed on the shaft portion and introducing the implant in the loaded position across an incision to an implantation site;
   wherein the distal side comprises a forward portion disposed distally from the implant-accommodating surface, the forward portion being elevated with respect to the implant-accommodating surface and including a tapered portion that is radially tapered with respect to the longitudinal axis from a low radial cross-section at the distal end of the shaft portion to a taller radial cross-section disposed towards the implant-mounting member such that the forward portion is configured for spreading tissue thereabout when the introducer is pushed therethrough.

2. The surgical introducer of claim 1, wherein the introducer is a gastric band introducer, and the implant-mounting member comprises a band-pulling member configured for pulling the band across an incision in an abdominal wall.

3. The surgical introducer of claim 2, further comprising a retaining member disposed on the proximal side and configured for engaging and retaining a portion of the band that is remote from the pulling member.

4. The surgical introducer of claim 3, wherein the retaining member extends radially from the shaft portion and defines a radial groove that is tapered to narrow towards the longitudinal axis for wedging said other portion of the band.

5. The surgical introducer of claim 4, wherein the retaining member protrudes radially and the radial groove is configured for receiving and releasably retaining a tail of the band, which is stretched longitudinally over the band-accommodating surface from the distal portion, wedged into engagement in the radial groove of the retaining member, the retaining member being positioned to remain outside the patient when the distal end is disposed inside the patient's abdomen.

6. The surgical introducer of claim 2, wherein the implant is a surgical band, and the implant-accommodating surface is a band-accommodating surface on an exterior of the shaft portion, the band-accommodating surface being disposed lower than the taller radial cross-section of the tapered portion and being shaped to provide a lowered radial profile of the band in the loaded position, in which the band is in a generally flat disposition against the band-accommodating surface.

7. The surgical introducer of claim 6, wherein the band-pulling member comprises a hook that extends from the band-accommodating surface to a height that is lower than the forward portion in a radial direction with respect to the longitudinal axis.

8. A surgical assembly, comprising:
the surgical introducer of claim 6; and
the implant, which comprises a gastric band which is configured for loading in the loaded position.

9. The surgical introducer of claim 6, wherein the band-accommodating surface is flattened in a lateral direction with a configuration for stabilizing the gastric band in the loaded position.

10. The surgical introducer of claim 9, wherein the band-accommodating surface defines a notch extending laterally with respect to the longitudinal axis, disposed proximally from the band-pulling member and configured, and dimensioned for receiving a band protrusion of the gastric band for reducing the protruding radial height of the gastric band above the shaft portion in the loaded position.

11. The surgical introducer of claim 10, wherein the notch comprises a plurality of notches for selectively accommodating a band protrusion of a size of band selected from a plurality of sizes of bands.

12. The surgical introducer of claim 10, wherein the band-pulling member comprises a seat that is engaged with the band in the loaded position for the pulling of the band, the notch being positioned to receive the band protrusion disposed between about 1 cm to 2 cm proximally of the pulling-member seat.

13. The surgical introducer of claim 10, wherein the pulling member comprises a hook that extends from the band-accommodating surface and the hook extends radially with respect to the longitudinal axis by a first height, and the forward portion extends radially with respect to the longitudinal axis by a second height that is at least as high as the first height to reduce or avoid catching the hook with the loaded implant on the surrounding tissue.

14. The surgical introducer of claim 9, wherein the pulling member comprises a hook that extends from the band-accommodating surface and comprises a distally facing tip that is radially spaced above the band-accommodating surface for hooking into an opening of the band.

15. The surgical introducer of claim 1, wherein the forward portion is radially eccentric with respect to the guide bore.

16. The surgical introducer of claim 1, wherein the tapered portion includes an insertion-assisting surface that is sloped towards the longitudinal axis in the distal direction and is flattened such that the insertion-assisting surface has a radial cross-section with lateral sides that are disposed further from the longitudinal axis than an intermediate portion of the insertion-assisting surface therebetween to spread connective tissue thereabout when the introducer is rotated about the longitudinal axis.

17. The surgical introducer of claim 16, wherein the insertion-assisting surface is substantially planar and is sloped to face radially and distally, the insertion-assisting surface being inclined closer to a radial direction than a distal direction, wherein the radial direction is substantially the same as a radial direction in which the band-accommodating surface faces.

18. The surgical introducer of claim 16, wherein the insertion-assisting surface is concave.

19. The surgical introducer of claim 16, wherein the insertion-assisting surface is sloped at an angle with respect to the longitudinal axis of between about 10° and 60°.

20. The surgical introducer of claim 16, wherein the insertion-assisting surface is sloped at an angle with respect to the longitudinal axis of between about 20° and 30°.

21. The surgical introducer of claim 16, wherein the insertion-assisting surface extends to substantially longitudinally adjacent to the distal opening at the distal end of the shaft.

22. The surgical introducer of claim 16, wherein the forward portion at the insertion-assisting surface is radially eccentric with respect to the guide bore longitudinal axis.

23. The surgical introducer of claim 1, wherein the bore defines a proximal opening at a proximal end of the shaft along the longitudinal axis through which the bore extends longitudinally with respect to the shaft portion, such that the guide member is receivable in the distal opening, through the bore, and exiting the proximal opening.

24. The surgical introducer of claim 1, further comprising the elongated guide member receivable through the distal opening and through the bore.

* * * * *